United States Patent
Kariya et al.

[11] Patent Number: 6,096,099
[45] Date of Patent: Aug. 1, 2000

[54] HAIR DYE COMPOSITION COMPRISING ACID DYES

[75] Inventors: Naohiro Kariya; Atsushi Nakashimada; Nozomi Hagashima; Yutaka Shibata; Masahiko Sakai; Hajime Miyabe, all of Tokyo, Japan

[73] Assignee: Kao Corporation, Tokyo, Japan

[21] Appl. No.: 09/316,361

[22] Filed: May 21, 1999

[30] Foreign Application Priority Data

May 26, 1998 [JP] Japan ................................. 10-144044

[51] Int. Cl.⁷ ...................................................... A61K 7/13
[52] U.S. Cl. .......................... 8/405; 8/435; 8/552; 8/561; 8/613
[58] Field of Search ................ 8/405, 435, 428, 8/552, 576, 561, 613

[56] References Cited

U.S. PATENT DOCUMENTS

| | | | |
|---|---|---|---|
| 3,630,654 | 12/1971 | Rossenthal et al. | 8/405 |
| 3,653,797 | 4/1972 | Reiss et al. | 8/405 |
| 3,933,422 | 1/1976 | Saad | 8/425 |
| 5,254,333 | 10/1993 | Kajino et al. | 8/405 |
| 5,356,438 | 10/1994 | Kim et al. | 8/405 |
| 5,595,197 | 1/1997 | Samain et al. | 8/405 |
| 5,601,620 | 2/1997 | Ishikawa | 8/405 |
| 5,750,099 | 5/1998 | Yoshihara et al. | 8/405 |
| 5,958,084 | 9/1999 | Shibata et al. | 8/408 |

FOREIGN PATENT DOCUMENTS

| | | |
|---|---|---|
| 0 161 073 | 11/1985 | European Pat. Off. . |
| 884044 | 12/1998 | European Pat. Off. . |
| WO 98 15256 | 4/1998 | WIPO . |

OTHER PUBLICATIONS

English language translation of Shiseido Co, JP 60109515, pp. 1–9, Jun. 1985.
Caplus Abstract of JP 5–279233, Sanyo Chemical Ind Ltd., Oct. 1993.
Caplus Abstract of JP 63–239209, Hoyu Co, Ltd., Oct. 1988.
Derwent Publications, 85–181163, JP 60 109515, Jun. 15, 1985.

*Primary Examiner*—Caroline D. Liott
*Attorney, Agent, or Firm*—Oblon, Spivak, McClelland, Maier & Neustadt, P.C.

[57] ABSTRACT

Disclosed herein is a hair dye composition comprising (A) benzyloxyethanol and/or benzyl alcohol, (B) propylene carbonate and (C) an acid dye and having a pH of 2.0 to 6.0. The composition has excellent hair-dyeing ability and good fastness to shampoo.

8 Claims, No Drawings

HAIR DYE COMPOSITION COMPRISING ACID DYES

BACKGROUND OF THE INVENTION

1. Field of the Invention

The present invention relates to a hair dye composition having excellent hair-dyeing ability and good fastness to shampoo.

2. Description of the Background Art

Acid hair dye compositions comprising an acid dye and various kinds of organic solvents as a penetrant solvent have heretofore been known (Japanese Patent Publication No. 23911/1973, and Japanese Patent Application Laid-Open Nos. 210023/1986 and 101841/1995). However, these hair dye compositions have been good in penetrability into hair, but insufficient in hair-dyeing ability and fastness to shampoo.

SUMMARY OF THE INVENTION

Accordingly, it is an object of the present invention to provide a hair dye composition having excellent hair-dyeing ability and good fastness to shampoo.

The present inventors have found that when 2 or 3 specific organic solvents are used in combination as a penetrant solvent, a hair dye composition having excellent hair-dyeing ability and good fastness to shampoo can be obtained, thus leading to completion of the present invention.

According to the present invention, there is thus provided a hair dye composition comprising (A) benzyloxyethanol and/or benzyl alcohol, (B) propylene carbonate and (C) an acid dye, and having a pH of 2.0 to 6.0.

The hair dye composition according to the present invention has excellent hair-dyeing ability and good fastness to shampoo.

DETAILED DESCRIPTION OF THE PREFERRED EMBODIMENTS

In the hair dye composition according to the present invention, the components (A) and (B) must be used in combination for enhancing the penetrability of the acid dye into hair. More specifically, when the components (A) and (B) are used in combination, the hair-dyeing ability and fastness to shampoo of the resulting hair dye composition are improved by leaps and bounds compared with the case where these components are used singly. In addition, the combined use of the components (A) and (B) can provides a composition having excellent hair-dyeing ability and fastness to shampoo compared with the case where a component similar to the component (A), for example, β-phenylethyl alcohol, is used, or where a component similar to the component (B), for example, ethylene carbonate. These components (A) and (B) are preferably incorporated in a proportion of 0.1 to 50% by weight, more preferably 1 to 50% by weight, most preferably 5 to 50% by weight in total, based on the total weight of the composition from the viewpoint of achieving a sufficient effect to dye the hair. A ratio of the component (A) to (B) is preferably within the range from 100:1 to 1:100.

No particular limitation is imposed on the acid dye of the component (C) so far as it is a water-soluble acid dye commonly used in the classical cosmetic compositions and the like. Examples thereof include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 203, Red Color No. 232, Green Color No. 204, Green Color No. 205, Red Color No. 401, Yellow Color No. 403(1), Green Color No. 401, Green Color No. 402, Black Color No. 401 and Purple Color No. 401.

These acid dyes may be used either singly or in any combination thereof and are preferably incorporated in a proportion of 0.001 to 5% by weight, more preferably 0.001 to 4.5% by weight, most preferably 0.001 to 4% by weight based on the total weight of the composition, from the viewpoint of practical use in that a sufficient effect to dye the hair is achieved, and the hand skin is scarcely smeared.

The hair dye composition according to the present invention must have a pH of 2.0 to 6.0, preferably 2.0 to 5.0, particularly preferably 2.5 to 4.0. If the pH is lower than 2.0, the resulting composition tends to undergo color migration to the scalp and hand skin and may roughen the scalp and hand skin due to an acid component in some cases. If the pH exceeds 6.0, the penetration accelerating effect on the acid dye is lowered.

Incidentally, the pH may be adjusted in accordance with a method known per se in the art. The adjustment of the pH to the above range permits facilitating the penetration of the acid dye into the hair. The acid used in the adjustment of the pH is preferably a weak acid because the hair itself has an ion exchange capability. Specific example thereof include organic acids such as citric acid, glycolic acid, succinic acid, tartaric acid, lactic acid, fumaric acid, malic acid, levulinic acid, butyric acid, valeric acid, oxalic acid, maleic acid and mandelic acid, and inorganic acids such as phosphoric acid. It is preferred that each of these weak acids be used in combination with its potassium salt, sodium salt, ammonium salt, triethanolamine salt or the like to impart a buffer capacity to the system.

This buffer capacity is preferably not lower than 0.007 gram equivalents/liter, but lower than 0.2 gram equivalents/liter, preferably not lower than 0.01 gram equivalents/liter, but lower than 0.2 gram equivalents/liter, more preferably not lower than 0.015 gram equivalents/liter, but lower than 0.2 gram equivalents/liter as the buffer capacity of a 10% aqueous solution of the hair dye composition. The buffer capacity in the present invention means a value determined by using, as a measure, the concentration of a base required to raise the pH of a 10% aqueous solution by 1 from the initial value thereof in accordance with the following equation:

$$\text{Buffer capacity} = |dC_B/dpH|$$

wherein $C_B$ is an ion concentration of the base (gram equivalent/liter).

The amount of the compound incorporated for imparting such a buffer capacity is not particularly specified and varies according to the kind of the compound for imparting the buffer capacity. For example, when sodium citrate is used as the compound for imparting the buffer capacity, the compound is incorporated at a concentration of at least about 1%.

The hair dye composition according to the present invention may further comprise (D) a water-soluble polymer. The incorporation of such a polymer is preferred in that the drooping of the resulting composition upon use can be prevented, and such a composition causes no smearing on the scalp and the like. No particular limitation is imposed on such a water-soluble polymer so far as it is a water-soluble polymer commonly used in the classical cosmetic compositions and the like. Examples thereof include gum arabic, carrageenan, karaya gum, tragacanth gum, carob gum, quince seed (marmelo), casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), poly (vinyl methyl ether) (PVM), polyvinyl pyrrolidone (PVP), sodium polyacrylate, locust bean gum, guar gum, tamarind gum, dialkyldimethylammonium cellulose sulfates, xanthan gum, modified xanthan gum, aluminum magnesium silicate and bentonite. Of these, hydroxyethyl cellulose, xanthan gum and modified xanthan gum are particularly preferred.

These water-soluble polymers may be used either singly or in any combination thereof and are preferably incorporated in a proportion of 0.1 to 10% by weight, particularly 0.5 to 5% by weight based on the total weight of the composition.

Into the hair dye composition according to the present invention, may also be incorporated a lower alcohol or lower polyol for the purpose of enhancing the solubility of the components (A) and (B). Specific examples thereof include those having 2 to 4 carbon atoms, such as ethanol, isopropanol, n-propanol, n-butanol, ethylene glycol, propylene glycol, isopropylene glycol, 1,3-butylene glycol and glycerol.

These lower alcohols and lower polyols may be used either singly or in any combination thereof and are preferably incorporated in a proportion of 0.1 to 30% by weight, particularly 0.1 to 20% by weight based on the total weight of the composition.

Besides the above components, components commonly used in the classical cosmetic compositions and the like, for example, surfactants, cationic polymers, oily substances, silicone derivatives, perfume bases, preservatives, ultraviolet absorbents, antioxidants, germicides, propellants, etc. may further be suitably incorporated into the hair dye composition according to the present invention so far as no detrimental influence is thereby imposed on the effects of the present invention. The hair dye composition according to the present invention can be prepared in accordance with a method known per se in the art.

In order to use the hair dye composition according to the present invention, it is only necessary to apply a proper amount of the hair dye composition to the hair with, for example, a comb or brush, leave the hair thus applied to stand for about 1 to 30 minutes after the application and then rinse the composition out of the hair.

EXAMPLE 1

Hair dye compositions for dyeing the hair in a light brown color having their corresponding compositions shown in Table 1 were prepared to evaluate them as to hair-dyeing ability and fastness to shampoo. The results are shown in table 1.

Preparation process

Organic solvent(s), an acid and an acid dye were added to purified water to uniformly dissolve the components therein, and hydroxyethyl cellulose or xanthan gum was added to the resultant solution to dissolve them therein. The pH of the thus-obtained solution was adjusted to pH 3.0 with aqueous caustic soda to obtain a hair dye composition.

Evaluation method

Each hair dye composition was applied to white tresses of goat hair (1 g), and the tresses were then left to stand for 15 minutes at 30° C. Thereafter, the tresses were washed with water, shampooed once and dried. With respect to the thus-treated tresses, 20 evaluators were got to evaluate the hair dye composition as to hair-dyeing ability in accordance with the following standard.

The tresses were then shampooed 10 times and dried. With respect to the thus-treated tresses, 20 evaluators were got to evaluate the hair dye composition as to fastness to shampoo in accordance with the following standard.

Evaluation standard:

⊚: At least 80% of the evaluators evaluated that hair-dyeing ability and fastness to shampoo were good;

○: 50% to lower than 80% of the evaluators evaluated that hair-dyeing ability and fastness to shampoo were good;

Δ: 20% to lower than 50% of the evaluators evaluated that hair-dyeing ability and fastness to shampoo were good;

X: Lower than 20% of the evaluators evaluated that hair-dyeing ability and fastness to shampoo were good.

TABLE 1

(% by weight)

| | Invention product | | | | | Comparative product | | | |
|---|---|---|---|---|---|---|---|---|---|
| Component | 1 | 2 | 3 | 4 | 5 | 1 | 2 | 3 | 4 |
| Black Color No. 401 | 0.8 | 0.8 | 0.8 | 0.16 | 0.16 | 0.8 | 0.8 | 0.8 | 0.8 |
| Orange Color No. 205 | 2.25 | 2.25 | 2.25 | 0.45 | 0.45 | 2.25 | 2.25 | 2.25 | 2.25 |
| Benzyloxyethanol | 0.2 | — | 0.1 | 10.0 | — | 0.05 | — | — | 0.02 |
| Benzyl alcohol | — | 0.25 | 0.1 | — | 10.0 | — | 0.05 | — | 0.03 |
| Propylene carbonate | 0.3 | 0.25 | 0.3 | 12.5 | 10.0 | — | — | 0.05 | — |
| Ethanol | — | — | — | 2.5 | 5.0 | — | — | — | — |
| Citric acid | — | — | — | 3.0 | 3.0 | — | — | — | — |
| Lactic acid | 3.0 | 3.0 | 3.0 | — | — | 3.0 | 3.0 | 3.0 | 3.0 |
| Caustic soda (48% aqueous solution) | Adjusted to pH 3.0 | | | | | Adjusted to pH 3.0 | | | |
| Hydroxyethyl cellulose | 1.0 | 1.0 | 1.0 | — | — | 1.0 | 1.0 | 1.0 | 1.0 |
| Xanthan gum | — | — | — | 1.0 | 1.0 | — | — | — | — |
| Purified water | Balance | Balance | Balance | Balance | Balance | Balance | Balance | Balance | Balance |
| Evaluation Hair-dyeing ability | ○ | ○ | ○ | ⊚ | ⊚ | Δ | Δ | x | Δ |

TABLE 1-continued

|  | Invention product | | | | | Comparative product | | | | (% by weight) |
|---|---|---|---|---|---|---|---|---|---|---|
| Component | 1 | 2 | 3 | 4 | 5 | 1 | 2 | 3 | 4 | |
| Fastness to shampoo | ○ | ○ | ○ | ⊙ | ⊙ | x | x | x | x | |

EXAMPLE 2

Hair dye compositions for dyeing the hair in a blue color having their corresponding compositions shown in Table 2 were prepared in the same manner as in Example 1 to evaluate them as to hair-dyeing ability and fastness to shampoo in the same manner as in Example 1. The results are shown in Table 2.

TABLE 2

|  | Invention product | | Comparative product | | (% by weight) |
|---|---|---|---|---|---|
| Component | 6 | 7 | 5 | 6 | |
| Black Color No. 401 | 0.001 | 0.001 | 0.001 | 0.001 | |
| Purple Color No. 401 | 0.002 | 0.002 | 0.002 | 0.002 | |
| Benzyloxyethanol | 20.0 | — | 20.0 | — | |
| Benzyl alcohol | — | 15.0 | — | 30.0 | |
| Propylene carbonate | 20.0 | 25.0 | 40.0 | 30.0 | |
| Ethanol | 5.0 | 5.0 | 5.0 | 5.0 | |
| Citric acid | — | 3.0 | — | 3.0 | |
| Lactic acid | 3.0 | — | 3.0 | — | |
| Caustic soda (48% aqueous solution) | Adjusted to pH 3.0 | | Adjusted to pH 3.0 | | |
| Hydroxyethyl cellulose | — | 1.0 | — | 1.0 | |
| Xanthan gum | 1.0 | — | 1.0 | — | |
| Purified water | Balance | Balance | Balance | Balance | |
| Evaluation Hair-dyeing ability | ○ | ○ | Δ | Δ | |
| Fastness to shampoo | ○ | ○ | Δ | Δ | |

EXAMPLE 3

Hair dye compositions for dyeing the hair in a light brown color having their corresponding compositions shown in Table 3 were prepared in the same manner as in Example 1 to evaluate them as to hair-dyeing ability and fastness to shampoo in the same manner as in Example 1. The results are shown in Table 3.

TABLE 3

|  | Invention product | | (% by weight) Comparative product |
|---|---|---|---|
| Component | 8 | 9 | 7 |
| Black Color No. 401 | 0.1 | 0.1 | 0.1 |
| Orange Color No. 205 | 0.4 | 0.4 | 0.4 |
| Benzyloxyethanol | 11.0 | — | — |
| Benzyl alcohol | — | 7.0 | 7.0 |
| Propylene carbonate | 19.0 | 23.0 | 23.0 |
| Ethanol | 5.0 | 5.0 | 5.0 |
| Citric acid | 1.0 | 1.0 | 1.0 |
| Lactic acid | 2.0 | 2.0 | 2.0 |
| Caustic soda (48% aqueous solution) | Adjusted to pH 3.0 | Adjusted to pH 5.0 | Adjusted to pH 7.0 |
| Hydroxyethyl cellulose | — | — | — |
| Xanthan gum | 1.0 | 1.0 | 1.0 |

TABLE 3-continued

|  | Invention product | | (% by weight) Comparative product |
|---|---|---|---|
| Component | 8 | 9 | 7 |
| Purified water | Balance | Balance | Balance |
| Evaluation Hair-dyeing ability | ⊙ | ○ | x |
| Fastness to shampoo | ⊙ | ○ | x |

EXAMPLE 4

Hair dye compositions having their corresponding compositions shown in Table 4 were prepared in the same manner as in Example 1 to evaluate them as to hair-dyeing ability and fastness to shampoo in the same manner as in Example 1. The results are shown in Table 4.

TABLE 4

|  | Invention product | | Comparative product | | (% by weight) |
|---|---|---|---|---|---|
| Component | 10 | 11 | 8 | 9 | |
| Black Color No. 401 | 0.18 | — | 0.18 | — | |
| Blue Color No. 201 | 0.02 | — | 0.02 | — | |
| Yellow Color No. 203 | — | 0.2 | — | 0.2 | |
| Red Color No. 106 | — | 0.7 | — | 0.7 | |
| Benzyloxyethanol | — | — | — | — | |
| Benzyl alcohol | 15.0 | 5.0 | 15.0 | — | |
| β-Phenylethyl alcohol | — | — | — | 5.0 | |
| Propylene carbonate | 35.0 | 7.0 | — | 7.0 | |
| Ethylene carbonate | — | — | 35.0 | — | |
| Ethanol | 5.0 | — | 5.0 | — | |
| Isopropanol | — | 20.0 | — | 20.0 | |
| Citric acid | — | 3.0 | — | 3.0 | |
| Lactic acid | 3.0 | — | 3.0 | — | |
| Caustic soda (48% aqueous solution) | Adjusted to pH 3.7 | Adjusted to pH 3.0 | Adjusted to pH 3.7 | Adjusted to pH 3.0 | |
| Hydroxyethyl cellulose | — | 1.0 | — | 1.0 | |
| Xanthan gum | 1.0 | — | 1.0 | — | |
| Purified water | Balance | Balance | Balance | Balance | |
| Evaluation Hair-dyeing ability | ○ | ⊙ | x | Δ | |
| Fastness to shampoo | ○ | ⊙ | x | Δ | |

Japanese Patent Application No. 10-144044 is incorporated herein by reference.

What is claimed is:

1. A hair dye composition comprising (A) benzyloxyethanol and/or benzyl alcohol, (B) propylene carbonate and (C) an acid dye, and having a pH of 2.0 to 6.0.

2. The hair dye composition according to claim 1, wherein the components (A) and (B) are contained in a proportion of 0.1 to 50% by weight in total, and the component (C) is contained in a proportion of 0.001 to 5% by weight.

3. The hair dye composition according to claim 1 or 2, which further comprises (D) a water-soluble polymer.

4. The hair dye composition of claim 1, wherein components (A) and (B) are contained in a proportion of 0.1 to 50% by weight based on the total weight of said composition.

5. The hair dye composition of claim 1, wherein a ratio of component (A) to (B) is within the range of 100:1 to 1:100.

6. The hair dye composition of claim 3, wherein said water-soluble polymer is selected from the group consisting of gum arabic, carrageenan, karaya gum, tragacanth gum, carob gum, quince seed, casein, dextrin, gelatin, sodium pectate, sodium alginate, methylcellulose, ethylcellulose, carboxymethyl cellulose, hydroxyethyl cellulose, hydroxypropyl cellulose, polyvinyl alcohol, poly(vinylmethylether), polyvinyl pyrrolidone, sodium polyacrylate, locust bean gum, guar gum, tamarind gum, dialkyldimethylammonium cellulose sulfates, xanthan gum, modified xanthan gum, aluminum magnesium silicate, bentonite and a mixture thereof.

7. The hair dye composition of claim 3, comprising said water-soluble polymer in an amount of 0.1–10% by weight, based on the total weight of said composition.

8. The hair dye composition of claim 1, further comprising a lower alcohol, a lower polyol or a mixture thereof.

* * * * *